United States Patent
Sakaguchi et al.

(10) Patent No.: US 6,776,821 B2
(45) Date of Patent: *Aug. 17, 2004

(54) FIXING MATERIAL FOR GASEOUS HYDROCARBON AND USE THEREOF, AND METHOD FOR SOLIDIFYING HYDROCARBON

(75) Inventors: Hiroshi Sakaguchi, Tsukuba (JP); Yoshishige Kida, Kashihara (JP); Seizi Iseki, Kashiwara (JP)

(73) Assignees: National Institute of Advanced Industrial Science and Technology, Tokyo (JP); Okamura Oil, Mill, Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/093,529

(22) Filed: Mar. 11, 2002

(65) Prior Publication Data

US 2002/0173686 A1 Nov. 21, 2002

(30) Foreign Application Priority Data

Mar. 14, 2001 (JP) ........................................ 2001-073198

(51) Int. Cl.$^7$ .............................. B01J 20/22; B01J 20/30
(52) U.S. Cl. ............................... 95/91; 95/143; 96/118; 585/3; 585/801
(58) Field of Search ............................... 95/90, 91, 114, 95/115, 143, 144, 148, 900; 96/108, 118; 502/526; 252/184; 585/3, 801, 932

(56) References Cited

U.S. PATENT DOCUMENTS 5,292,707 A * 3/1994 Aparicio et al. ............ 502/418
6,417,415 B1 * 7/2002 Sakaguchi et al. ............ 585/3
6,570,045 B2   5/2003 Sakaguchi et al.

FOREIGN PATENT DOCUMENTS

| JP | 55-75493 A | | 6/1980 |
| JP | 56-157492 A | | 12/1981 |
| JP | 59-142274 A | | 8/1984 |
| JP | 60-67422 A | | 4/1985 |
| JP | 60-130543 A | | 7/1985 |
| JP | 62-265393 A | | 11/1987 |
| JP | 64-4350 A | | 1/1989 |
| JP | 1-174595 A | | 7/1989 |
| JP | 1-201394 A | | 8/1989 |
| JP | 6-17069 A | * | 1/1994 |
| JP | 6-55069 A | | 3/1994 |
| JP | 7-82209 A | | 3/1995 |
| JP | 9-253656 A | | 9/1997 |
| JP | 2000-86541 A | * | 3/2000 |
| JP | 2000-143997 A | | 5/2000 |
| JP | 2001-48811 A | | 2/2001 |
| JP | 2001-048811 A | * | 2/2001 |
| JP | 2001-72617 A | | 3/2001 |
| JP | 2002-64215 A | * | 3/2001 |
| JP | 2002-265982 A | | 9/2002 |
| JP | 2002-265984 A | | 9/2002 |
| JP | 2002-273216 A | | 9/2002 |
| JP | 2002-273217 A | | 9/2002 |

* cited by examiner

*Primary Examiner*—Frank M. Lawrence
(74) *Attorney, Agent, or Firm*—Birch, Stewart, Kolasch & Birch, LLP

(57) ABSTRACT

A material for fixing gaseous hydrocarbon containing fibrous crystal aggregates formed by precipitating by making a metal aliphatic carboxylate dissolve completely in pure water to give a solution, stirring and gradually cooling the resulting solution; a method of preparing the fixing material; and a method of adsorbing and solidifying gaseous hydrocarbon by using the fixing material.

8 Claims, 2 Drawing Sheets

0.1 mm 0.1 mm

FIXING MATERIAL FOR GASEOUS HYDROCARBON AND USE THEREOF, AND METHOD FOR SOLIDIFYING HYDROCARBON

FILED OF THE INVENTION

The present invention relates to a fixing material for gaseous hydrocarbon for efficiently fixing gaseous hydrocarbon; to a method of preparing the same; and to a method of fixing gaseous hydrocarbon by using the fixing material.

BACKGROUND OF THE INVENTION

As the scale of petrochemical industry and natural gas industry is enlarging year by year and mass production and mass consumption of organic compounds are conducted for organic compound, environmental pollution and accidents threatening the existence of human beings and living things, such as large fires and explosions attributable to accidents in various chemical factories, petrochemical complexes, tankers, trucking, pipelines and the like, occur frequently worldwide. Accordingly safe handling and suitable treating during transportation or storage of organic compounds including petrochemical materials, particularly gaseous hydrocarbon are critical problems. One of fundamental measures against these explosions, fires and leakage accidents is that a large amount of gaseous hydrocarbon and mixtures thereof handled in various chemical industries, petrochemical complexes and trucking and storage facilities are converted into safe solids and returned if necessary to the original gaseous one. It is thought that by conversion thereof into safe solids easy to handle, many accidents would be prevented, and huge and often dangerous storage facilities, pipelines, trucking, freezing or thermally insulating facilities could be significantly modified.

In consideration of these aspects, there is demand for development of a method wherein a wide variety of gaseous hydrocarbon and mixed gas handled in various chemical factories, petrochemical complexes and trucking and storage facilities are fixed easily and converted into safe solids, and then returned if necessary to the original gaseous hydrocarbon. Conversion of gaseous hydrocarbon into other safe materials by a certain chemical reaction does not solve the problem, and a method accompanying chemical reaction should be avoided.

Accordingly, a method of solidifying gaseous hydrocarbon as it is by a physicochemical means is considered most preferable.

The requirements for a material for solidifying gaseous hydrocarbon include (1) gaseous hydrocarbon can be fixed and solidified easily at low temperatures without damaging reaction units in a factory, and from the solidified complex, the original gaseous hydrocarbon can be easily recovered, and further the recovered fixing material can be used through recycling, (2) the material is chemically relatively stable, and (3) the material is supposed to be used in a large quantities, and should thus be a safe and nontoxic substance, and even if the material flows outside of the reaction unit and hardly recovered, the material itself is least dangerous to living things in the environment and to the environment.

Such physicochemical adsorbing materials are still not put to practical use, and there are few proposals including those at the experimental stage.

SUMMARY OF THE INVENTION

The present invention resides in a material for fixing gaseous hydrocarbon, which comprises fibrous crystal aggregates formed by precipitating by making a metal aliphatic carboxylate dissolve completely in pure water to give a solution, stirring, and gradually cooling the solution.

Further, the present invention resides in a material for fixing gaseous hydrocarbon, which comprises fibrous crystal aggregates formed by precipitating by making a metal aliphatic carboxylate dissolve completely in pure water to give a solution, adding an aqueous solution of an inorganic salt containing the same metal as in the metal aliphatic carboxylate, stirring, and gradually cooling the solution.

Further, the present invention resides in a method of solidifying gaseous hydrocarbon, which comprises the step of: fixing gaseous hydrocarbon, by using the fixing material comprising fibrous crystal aggregates as described above.

Further, the present invention resides in a method of solidifying gaseous hydrocarbon, which comprises the steps of: heating a solidified complex containing fixed gaseous hydrocarbon, obtained by the method described above, to decompose and separate the fixed material into its original metal aliphatic carboxylate and gaseous hydrocarbon; and recovering them.

Further, the present invention resides in a method of preparing a material for fixing gaseous hydrocarbon, which comprises the steps of: making a metal aliphatic carboxylate dissolve completely in pure water to give a solution; stirring; and gradually cooling the solution, thereby precipitating as fibrous crystal aggregates.

Further, the present invention resides in a method of preparing a material for fixing gaseous hydrocarbon, which comprises the steps of: making a metal aliphatic carboxylate dissolve completely in pure water to give a solution; adding an aqueous solution of an inorganic salt containing the same metal as in the metal aliphatic carboxylate; stirring; and gradually cooling the solution, thereby precipitating as fibrous crystal aggregates.

Other and further features and advantages of the invention will appear more fully from the following description, taken in connection with the accompanying drawings.

DETAILED DESCRIPTION OF THE INVENTION

Figure 1:
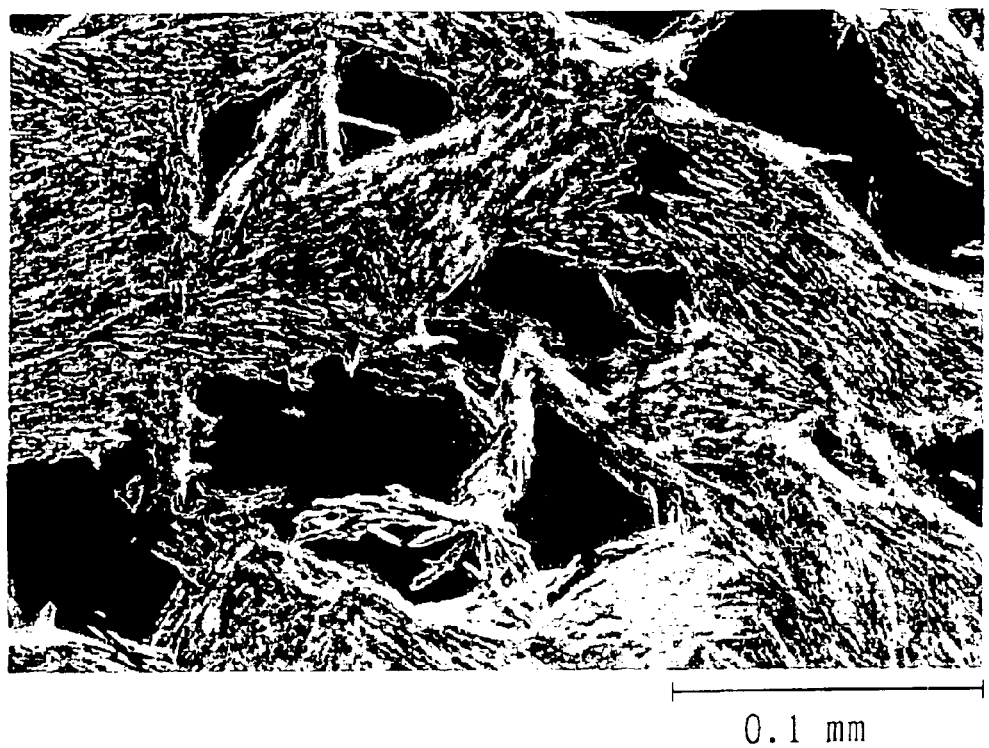
FIG. 1 is a microphotograph of the fibrous crystal aggregates obtained in Example 1.

The present inventors have studied the dissolution, emulsification and dispersion behavior, in water, of aliphatic carboxylic acid type compounds (particularly metal carboxylates) having alkyl groups of various lengths.

As a result, we have found that these carboxylic acid type compounds are dissolved completely in water at a high temperature; the compounds after completely dissolved can be maintained in a completely dissolved state even if an aqueous solution of an inorganic salt, such as sodium chloride, is added thereto at a high temperature; by stirring and gradually cooling the compounds in a completely dissolved state, the carboxylic acid type compounds are precipitated, for the first time, as fine and uniform fibrous crystal aggregates; and such fibrous crystal aggregates can particularly efficiently adsorb and solidify various gaseous hydrocarbon. The present invention is accomplished by further studies based on these findings.

According to the present invention, there are provided the following means:

(1) A material for fixing gaseous hydrocarbon, which comprises fibrous crystal aggregates formed by precipitating by making a metal aliphatic carboxylate dissolve completely in pure water to give a solution, stirring, and gradually cooling the solution;

(2) A material for fixing gaseous hydrocarbon, which comprises fibrous crystal aggregates formed by precipitating by making a metal aliphatic carboxylate dissolve completely in pure water to give a solution, adding an aqueous solution of an inorganic salt, such as sodium chloride, containing the same metal as in the metal aliphatic carboxylate, stirring, and gradually cooling the solution;

(3) A method of solidifying gaseous hydrocarbon, which comprises the step of: fixing gaseous hydrocarbon, by using the material comprising fibrous crystal aggregates according to the above (1) or (2);

(4) A method of solidifying gaseous hydrocarbon, which comprises the steps of: heating a solidified complex containing fixed gaseous hydrocarbon, obtained by the method according to the above (3), to decompose and separate the fixed material into its original metal aliphatic carboxylate and gaseous hydrocarbon; and recovering them;

(5) A method of preparing a material for fixing gaseous hydrocarbon, which comprises the steps of: making a metal aliphatic carboxylate dissolve completely in pure water to give a solution, stirring, and gradually cooling the solution, thereby precipitating as fibrous crystal aggregates; and (6) A method of preparing a material for fixing gaseous hydrocarbon, which comprises the steps of: making a metal aliphatic carboxylate dissolve completely in pure water to give a solution, adding an aqueous solution of an inorganic salt, such as sodium chloride, containing the same metal as in the metal aliphatic carboxylate, stirring, and gradually cooling the solution, thereby precipitating as fibrous crystal aggregates.

The fibrous crystal aggregates used in the present invention are aggregates of innumerable fine fibrous crystals, and the thickness of one fibrous crystal is preferably 1 μm or less, and the length thereof is preferably 50 to 1000 μm, more preferably 100 to 500 μm. Further, one fibrous crystal is composed of a large number of finer fibrous crystals.

As used herein, the gaseous hydrocarbon refers to that in the form of gas at ordinary temperature (20° C.) at normal pressure (0.1 MPa).

In the present invention, the crystals comprising fibrous aggregates acting as a material for fixing gaseous hydrocarbon are formed by heating and dissolving a metal aliphatic carboxylate in pure water, or dissolving a metal aliphatic carboxylate in pure water and then adding an aqueous solution of an inorganic salt such as a sodium salt (e.g., sodium chloride, sodium sulfate, sodium carbonate and the like), a potassium salt (e.g., potassium chloride and the like), or a lithium salt (e.g., lithium chloride and the like) containing the same metal as in the metal aliphatic carboxylate, followed by stirring and gradual cooling thereof. The fibrous crystal aggregates are maintained stably in a dispersed state for a long period usually at room temperature or less. Further, in this invention, solidification means that gaseous hydrocarbon is solidified by forming a complex with the fibrous crystal aggregates.

The metal aliphatic carboxylate (hereinafter which can be referred to as metal carboxylate) used in production of the fixing material in the present invention is a metal carboxylate preferably having a linear alkyl chain. The number of carbon atoms of the metal carboxylate is preferably 6 to 30, more preferably 8 to 22 and furthermore preferably 10 to 18. The metal thereof is preferably sodium, potassium or lithium, more preferably sodium or potassium. That is, the alkyl chain should have such suitable length that the metal carboxylate is completely dissolved in pure water by heating, and then stirred and gradually cooled as it is or after addition of an aqueous solution of an inorganic salt such as sodium chloride and the like containing the same metal as in the metal aliphatic carboxylate, whereby the metal carboxylate can be precipitated in a fibrous form.

In the case of a sodium carboxylate having a linear alkyl group where the number of carbon atoms is 6 to 10, it may be necessary to increase a concentration of the added sodium chloride or hydrated sodium sulfate or to cool thereof at room temperature or less. When the number of carbon atoms is 19 or more, it is necessary to put the temperature up to 100° C. or more or to decrease the concentration of sodium chloride, in order to dissolve the compound completely.

This also applies to a potassium or lithium carboxylate having a liner alkyl group.

The examples of the metal carboxylate include, for example, sodium octanoate, sodium nonanoate, sodium decanoate, sodium undecanoate, sodium dodecanoate, sodium tridecanoate, sodium tetradecanoate, sodium pentadecanoate, sodium hexadecanoate, sodium heptadecanoate, sodium octadecanoate, potassium tetradecanoate, potassium hexadecanoate, potassium octadecanoate, lithium hexadecanoate and the like.

Sodium aliphatic carboxylates have been used as soap for a long time, and their safety is proven. Potassium aliphatic carboxylates have also been used widely as medicated soap, and their safety is also proven. Further, lithium aliphatic carboxylates have also been industrially used, and their safety is confirmed. Further, sodium and potassium are contained originally in the seawater in large quantities, and even if they flow and remain in the sea, the environment will not be adversely affected. Further, sodium and potassium are also contained at various concentrations in rivers, lakes and marshes, and even if they flow and remain at usual concentrations, the environment will not be adversely affected.

The aqueous solution of sodium chloride used in the above is produced by dissolving various amounts of crystals of sodium chloride in pure water to give a solution. The aqueous solution is generally effective at concentrations ranging from a low concentration where sodium is slightly dissolved in water to the upper limit of the solubility thereof, but it is essential that depending on combination with the metal carboxylate, the concentration of the aqueous solution is high enough for crystals to be precipitated as fibrous aggregates, and the precipitated fibrous crystal aggregates are reacted with gaseous hydrocarbon. Further, sodium chloride is not always necessary to be pure, and sodium chloride present as a constituent component of seawater or natural water and nontoxic to humans and other living things may be dissolved at a concentration where the dissolved carboxylate can be precipitated. This also applies to other inorganic metal salts.

In the method of preparing the fixing material according to the present invention, it is particularly important that first the metal carboxylate described above is completely dissolved in pure water, and if necessary an aqueous solution containing metal ions is added thereto and completely mixed therewith, followed by stirring and gradual cooling thereof, whereby crystals are precipitated as fibrous aggregates in the aqueous solution. By using the crystals as fibrous aggregates, gaseous hydrocarbon can be adsorbed and solidified very effectively, and the complex thus formed can be recovered as mass. It is considered that the crystals as fibrous aggregates of the metal carboxylate have a large surface area to permit gaseous hydrocarbon to be efficiently adsorbed, and the materials which have adsorbed the gaseous hydrocarbon are attracted to one another via van der Waals force, to grow finally as spherical solid materials.

In the process of the present invention, the embodiments for preparing a material for solidifying gaseous hydrocarbon, which is comprised of fibrous crystal aggregates, are as follows:

(1) A process wherein a metal carboxylate is added to pure water, completely dissolved by heating, and cooled gradually to room temperature under vigorous stirring;

(2) A process wherein a metal carboxylate is added to pure water and completely dissolved by heating, and after an aqueous solution of sodium chloride, which has been heated in advance, is added thereto, the mixture is cooled gradually to room temperature under vigorous stirring;

(3) A process wherein an aqueous solution of various metal salts is used in place of the aqueous solution of sodium chloride in the above process (2); and (4) A process wherein after the solution is cooled to room temperature in the above process (2) or (3), the solution is further kept at about 0° C. for a long time, to precipitate crystals comprising fibrous aggregates.

Further, there is (5) a process wherein crystals of mixed fibrous aggregates of plural types of carboxylates are precipitated by using the processes (1) to (4).

In order to prepare the fixing materials, the molar ratio of metal carboxylate/water in precipitating the fibrous crystal aggregates is preferably from 0.1/1000 to 10/1000, more preferably from 0.5/1000 to 2/1000. Further, the molar ratio of inorganic metal salt/water during precipitation of the fibrous crystal aggregates is preferably from 0/1000 to the saturation concentration during heating.

In this case, first, heating is carried out in this invention in order to dissolve the carboxylate completely in pure water. The heating temperature is varied depending on the type of metal carboxylate used, and for example sodium carboxylates ranging from sodium pentadecanoate to octadecanoate are heated at 90 to 99° C. for about 30 minutes. Carboxylates having a shorter chain may be heated at further lower temperatures. Carboxylates having a longer chain should be heated at a high temperature of 100° C. or more in a pressure-resistant vessel in some cases. In either case, after the metal carboxylate is completely dissolved by heating, the resulting solution is vigorously stirred; or after a heated aqueous solution of sodium chloride or an aqueous solution of various metal salts is added, the mixture is vigorously stirred. Vigorous stirring is continued until the temperature of the solution is lowered to room temperature.

In the manner described above, very fine and fibrous crystal aggregates can be precipitated.

The fibrous crystal aggregates thus formed can be separated from the aqueous solution of sodium chloride and the like by a usual means such as centrifugation and the like or scooping the fibrous crystal aggregates up from the aqueous solution of metal salts, but usually the fibrous crystal aggregates are used in the aqueous dispersion as it is. Once formed, the fibrous crystal aggregates are very stable and usually maintained stably even at room temperature for a long time or even at high temperatures. For example, fibrous crystal aggregates obtained from sodium pentadecanoate are very stable usually at about −100 to 60° C.

The fixing material described above adsorbs gaseous hydrocarbon selectively by, for example, only introducing gaseous hydrocarbon and then stirring gently. Unless the ratio of gaseous hydrocarbon to the fibrous crystal aggregates is too high, substantially all gaseous hydrocarbon are adsorbed to float on the water. The fibrous crystal aggregates after having adsorbed gaseous hydrocarbon are in the form of fine particle complex when the ratio of gaseous hydrocarbon is low, while the ratio of gaseous hydrocarbon by weight is higher by several times than the fibrous crystal aggregates, the aggregates float on the water as a whole spherical mass. The mass can be easily scooped up from the water.

The examples of the hydrocarbon which can be adsorbed and solidified by the fixing material of the present invention include n-butane, isobutane, 1-butene, cis-2-butene, trans-2-butene, 1,3-butadiene, propane and propylene.

Further, in the present invention, a small amount of liquid hydrocarbon may be added to facilitate adsorption and solidification of gaseous hydrocarbon. The examples of the liquid hydrocarbon used include all n-paraffin ranging from n-pentane to hexadecane in a liquid state at room temperature, branched paraffin, olefin, alicyclic paraffin such as cyclohexane and the like, aromatic hydrocarbon such as benzene, toluene, xylene and the like, and mixed hydrocarbon such as light oil, kerosene, liquid paraffin and the like, but in consideration of easy handling, decomposition and recovery after fixation, unstable olefins and mixed hydrocarbon may not be used, and paraffin type hydrocarbon, alicyclic paraffin and aromatic hydrocarbon having a relative simple and stable structure are preferably used.

Depending on the type of gaseous hydrocarbon to be fixed in the case of only gaseous hydrocarbon, 1 g of the fibrous crystal aggregates of the present invention can usually adsorb gaseous hydrocarbon in an amount of 10 to 20 g. Further, in the case of the combination of gaseous hydrocarbon with liquid hydrocarbon, the fixed gaseous hydrocarbon can be significantly stabilized and thus adsorbed usually in an amount of 10 to 30 g by 1 g of the fibrous crystal aggregates of this invention.

To allow the fibrous crystal aggregates of the present invention to adsorb and fix gaseous hydrocarbon, the fibrous crystal aggregates may be contacted with gaseous hydrocarbon preferably for 1 minute or more, more preferably with gentle shaking.

Generally, the solid complexes formed after fixing only gaseous hydrocarbon have a slightly higher vapor pressure than the atmospheric pressure, and should thus be stored in a sealed container. Accordingly, in order to obtain the original gaseous hydrocarbon, the solidified complexes may be released at ordinary temperature at atmospheric pressure to recover the gaseous hydrocarbon in a conventional method. Generally, the solidified complexes formed after fixing gaseous hydrocarbon together with liquid hydrocarbon have a lower vapor pressure than the atmospheric pressure, so it is not always necessary to store the solid complexes in a sealed container, but for securing safety, the complexes are stored desirably in a simple sealed container. Accordingly, in this case, in order to obtain the original gaseous hydrocarbon, the solidified complexes may be heated at about 40 to 60° C. and released to recover in a conventional method. Either case, the complexes can be separated easily into their components i.e. the metal carboxylate, gaseous hydrocarbon, and liquid hydrocarbon (when used in combination). The metal carboxylate is separated and transferred to the aqueous phase.

The material for fixing gaseous hydrocarbon according to the present invention can efficiently adsorb and solidify mainly C3 to C4 hydrocarbons selectively. The fibrous crystal aggregates of the present invention can adsorb and fix gaseous hydrocarbon thereby forming solidified complexes which can be maintained stably in a simple container. The fixing material of the present invention is composed of only a very safe metal aliphatic carboxylate and an aqueous solution of a metal salt, and can thus prevent a pollution of the environment caused by the fixing material itself, explosions, fires and the like. Further, the fibrous crystal aggregates used in the present invention can be maintained stably in a dispersed state of fibrous crystal aggregates for a long period at room temperature, to make handling easy, and in the case where both gaseous hydrocarbon and liquid hydrocarbon have been fixed, the hydrocarbon can be separated by simple heating into the metal carboxylate, gaseous hydrocarbon and liquid hydrocarbon, and the metal carboxylate can be repeatedly utilized for solidification of gaseous hydrocarbon.

The solidifying method of the present invention is suitable for safe handling of gaseous hydrocarbon. Further, the solidifying method of the present invention can efficiently solidify gaseous hydrocarbons physicochemically.

The present invention will be described in more detail based on examples given below, but the present invention is not limited by these examples.

EXAMPLES

Example 1

132 mg (0.0005 mole) sodium pentadecanoate of high purity (99% or more) and 4.5 ml (0.25 mole) pure water were weighed and placed in a glass vessel, sealed and heated at 95° C., whereby the sodium pentadecanoate was completely dissolved. Separately, an aqueous solution prepared by completely dissolving 58.5 mg (0.010 mole) sodium chloride in 4.5 ml (0.25 mole) pure water was heated at 95° C. Both the solutions were mixed at 95° C., and immediately the mixture was vigorously stirred. The mixture was stirred for about 20 minutes during which the mixture was cooled to room temperature, whereby very fine and uniform fibrous crystal aggregates were precipitated throughout the solution. By leaving it at room temperature for 1 day, the fibrous crystal aggregates were made more stable and tried to gather on the water by attraction of the aggregates to one another in the form of fine crystals, and thus the aqueous solution become slightly colorless and transparent in a lower part. A microphotograph of the fibrous crystal aggregates of sodium pentadecanoate thus prepared is shown in FIG. 1 (×40).

The liquid in which the fibrous crystal aggregates were dispersed was cooled to about −10 to −20° C. with a freezing mixture of ice and sodium chloride, and after 2 g n-butane was added, the mixture was placed in a sealed vessel, and while the temperature of the mixture was returned to room temperature, the mixture was gently stirred whereby n-butane was immediately adsorbed into the fibrous crystal aggregates, to form white and spherical complexes as a whole, while an aqueous solution of sodium chloride was separated from the liquid in which the fibrous crystal aggregates were dispersed. The separated aqueous solution of sodium chloride was free of sodium pentadecanoate and n-butane and completely colorless and transparent. Further, the spherical complexes contained little water.

The vapor pressure of the resultant n-butanecontaining spherical complexes was slightly higher than the atmospheric pressure, so the complex initiated to boil when the vessel was opened, and boiling continued until butane disappeared.

Example 2

The same procedure as in Example 1 was conducted except that 139 mg (0.0005 mole) sodium hexadecanoate was used in place of sodium pentadecanoate, and as a result, uniform fibrous crystal aggregates were similarly obtained. 1.5 g n-butane was added thereto, and the mixture was gently shaken to form stable and spherical complexes, and the separated aqueous solution of sodium chloride was also colorless and transparent.

Example 3

The same procedure as in Example 1 was conducted except that two kinds of aqueous solutions which were different in concentration of sodium chloride were used in place of the aqueous solution of sodium chloride, and as a result, the same result was obtained when a quantity of the n-butane was from 10 to 15 times in weight ratio.

Example 4

The same procedure as in Example 1 was conducted except that 0.0005 mole of sodium undecanoate, sodium dodecanoate, sodium tridecanoate, sodium tetradecanoate, sodium heptadecanoate or sodium octadecanoate was used respectively in place of sodium pentadecanoate, and as a result, stable complexes were obtained when the n-butane to sodium carboxylate was from 10 to 30 times in weight ratio, respectively, to float on each colorless and transparent aqueous solution of sodium chloride.

Example 5

Figure 2:
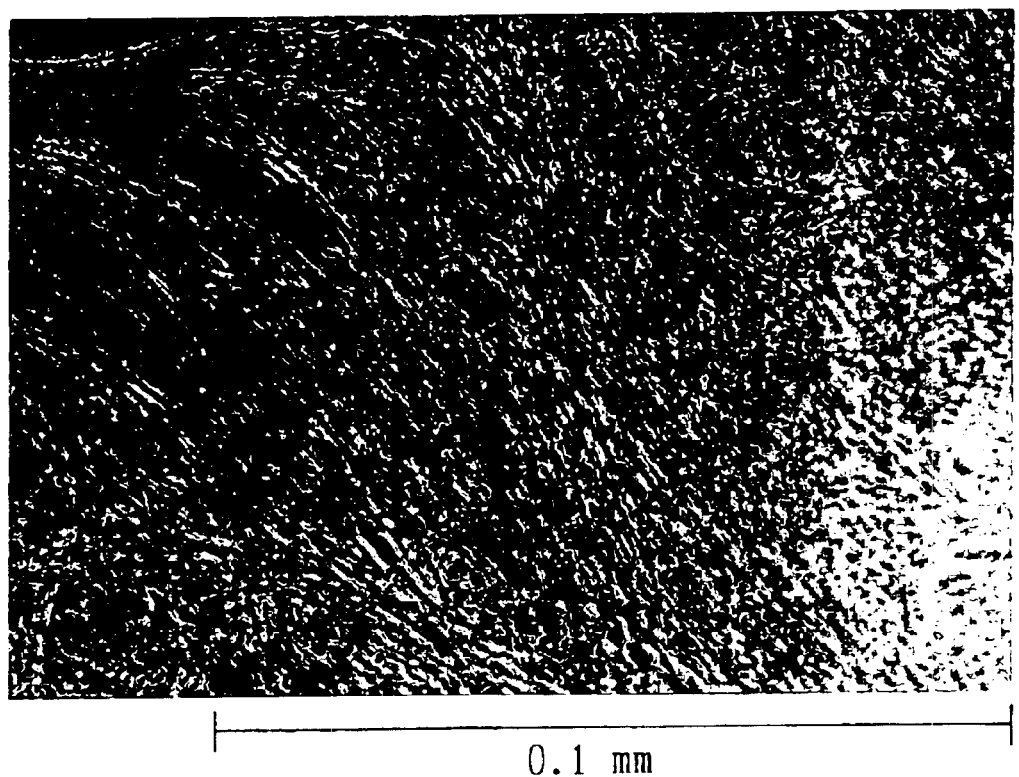
FIG. 2 is a microphotograph of the fibrous crystal aggregates obtained in Example 5.

The same procedure as in Example 1 was conducted except that 0.0005 mole of sodium decanoate was used in place of sodium pentadecanoate, and as a result, no fibrous crystal aggregates were precipitated even after an aqueous solution of sodium chloride was added thereto, stirred and left at room temperature. Accordingly, the mixture was further kept at 4° C. for one day, and as a result, similar fibrous crystal aggregates were precipitated, and the aggregates thus precipitated were stable for a long time even at room temperature. A microphotograph (×100) of the fibrous crystal aggregates of sodium pentadecanoate thus prepared is shown in FIG. 2. Similarly to Example 1, n-butane was added to the liquid in which the fibrous crystal aggregates were dispersed, and as a result, n-butane could be fixed in weight ratio of 20 times to the sodium decanoate, to form spherical complexes.

Example 6

The same procedure as in Examples 1, 3 and 4 was conducted except that isobutane, 1-butene, cis-2-butene, trans-2-butene, 1,3-butadiene, propane or propylene was used respectively in place of n-butane, and as a result, each one could be fixed and formed into spherical complexes until the ratio thereof to sodium pentadecanoate was from 10 to 30 times in weight ratio. The remaining aqueous solution remained colorless and transparent or slightly opaque. By releasing these complexes at ordinary temperature at atmospheric pressure, the original hydrocarbon component could be easily recovered.

Example 7

In Examples 1 to 6, a liquid hydrocarbon n-heptane or n-tetradecane together with gaseous hydrocarbon was added in a weight ratio of 5 to 20 times to the fibrous crystal aggregates, and as a result the gaseous hydrocarbon was fixed in a weight ratio of 10 to 30 times to the fibrous crystal aggregates, to obtain rigid spherical complexes. The remaining aqueous solution was colorless and transparent or slightly opaque. Further, these complexes could be stably present at ordinary temperature even if by releasing at atmospheric pressure. Accordingly, it is necessary to heat the complexes at about 40 to 60° C. in order to separate them into the components i.e. the fibrous crystal aggregates (actually in the form of honeycomb- or pumice stone-like porous complexes containing a very small amount of the liquid hydrocarbon), the liquid hydrocarbon, the gaseous hydrocarbon, and the aqueous solution.

Having described our invention as related to the present embodiments, it is our intention that the invention not be limited by any of the details of the description, unless otherwise specified, but rather be construed broadly within its spirit and scope as set out in the accompanying claims.

What is claimed is:

1. A material for fixing gaseous hydrocarbon, which comprises fibrous crystal aggregates formed by precipitating by making a metal aliphatic carboxylate dissolve completely in pure water to give a solution, stirring, and gradually cooling the solution.

2. A method of solidifying gaseous hydrocarbon, which comprises the step of: fixing gaseous hydrocarbon, by using the fixing material comprising fibrous crystal aggregates according to claim 1.

3. A method of solidifying gaseous hydrocarbon, which comprises the steps of: heating a solidified complex containing fixed gaseous hydrocarbon, obtained by the method according to claim 2, to decompose and separate solidified complex into its original metal aliphatic carboxylate and gaseous hydrocarbon; and recovering them.

4. A material for fixing gaseous hydrocarbon, which comprises fibrous crystal aggregates formed by precipitating by making a metal aliphatic carboxylate dissolve completely in pure water to give a solution; adding an aqueous solution of an inorganic salt containing the same metal as in the metal aliphatic carboxylate; stirring; and gradually cooling the solution.

5. A method of solidifying gaseous hydrocarbon, which comprises the step of: fixing gaseous hydrocarbon by using the fixing material comprising fibrous crystal aggregates according to claim 4.

6. A method of solidifying gaseous hydrocarbon, which comprises the steps of: heating a solidified complex containing fixed gaseous hydrocarbon, obtained by the method according to claim 5, to decompose and separate the solidified complex into its original metal aliphatic carboxylate and gaseous hydrocarbon; and recovering them.

7. A method of preparing a material for fixing gaseous hydrocarbon, which comprises the steps of: making a metal aliphatic carboxylate dissolve completely in pure water to give a solution; stirring; and gradually cooling the solution, thereby precipitating as fibrous crystal aggregates.

8. A method of preparing a material for fixing gaseous hydrocarbon, which comprises the steps of: making a metal aliphatic carboxylate dissolve completely in pure water to give a solution; adding an aqueous solution of an inorganic salt containing the same metal as in the metal aliphatic carboxylate; stirring; and gradually cooling the solution, thereby precipitating as fibrous crystal aggregates.

* * * * *